United States Patent
Margalit et al.

(10) Patent No.: US 11,890,229 B2
(45) Date of Patent: Feb. 6, 2024

(54) LASER DOSAGE DETERMINATION BY TEMPERATURE MONITORING

(71) Applicant: LUTRONIC VISION INC., Burlington, MA (US)

(72) Inventors: Mordehai Margalit, Zikhron Ya'akov (IL); Dayan Ban, Waterloo (CA)

(73) Assignee: LUTRONIC VISION INC.

(*) Notice: Subject to any disclaimer, the term of this patent is extended or adjusted under 35 U.S.C. 154(b) by 0 days.

(21) Appl. No.: 16/759,291

(22) PCT Filed: Oct. 25, 2017

(86) PCT No.: PCT/US2017/058331
§ 371 (c)(1),
(2) Date: Apr. 24, 2020

(87) PCT Pub. No.: WO2019/083525
PCT Pub. Date: May 2, 2019

(65) Prior Publication Data
US 2021/0161704 A1    Jun. 3, 2021

(51) Int. Cl.
*A61F 9/008* (2006.01)
*G01K 13/20* (2021.01)

(52) U.S. Cl.
CPC ........... *A61F 9/008* (2013.01); *G01K 13/20* (2021.01); *A61F 2009/00844* (2013.01)

(58) Field of Classification Search
None
See application file for complete search history.

(56) References Cited

U.S. PATENT DOCUMENTS

| | | | | |
|---|---|---|---|---|
| 5,354,323 A | * | 10/1994 | Whitebook | A61B 18/20 606/11 |
| 6,464,692 B1 | * | 10/2002 | Ruiz | G03F 7/70291 606/4 |
| 2004/0039378 A1 | * | 2/2004 | Lin | A61F 9/008 606/6 |
| 2012/0022510 A1 | * | 1/2012 | Welches | A61B 18/22 606/14 |

(Continued)

OTHER PUBLICATIONS

"Characteristics and Use of Infrared Detectors," Solid State Division, Technical Information SD-12, pp. 1-43 (2004).

(Continued)

*Primary Examiner* — Nathan J Jenness
*Assistant Examiner* — Skylar Lindsey Christianson

(57) ABSTRACT

In some examples, a laser-based ophthalmological surgical system includes a therapeutic radiation source, one or more optical elements, and a detector system. The therapeutic radiation source may be configured to emit therapeutic radiation. The one or more optical elements may be configured to direct the therapeutic radiation to a targeted area of an eye of a patient. A temperature of the targeted area may depend on a dosage of the therapeutic radiation. The detector system may be configured to measure thermal radiation emitted by the targeted area responsive to exposure to the therapeutic radiation. The one or more optical elements may be configured to optically couple the detector system to the targeted area.

10 Claims, 10 Drawing Sheets

(56) References Cited

U.S. PATENT DOCUMENTS

| | | | |
|---|---|---|---|
| 2012/0150160 A1* | 6/2012 | Vogler | A61F 9/00836 |
| | | | 606/4 |
| 2014/0160432 A1 | 6/2014 | Brown, Jr. et al. | |
| 2015/0131700 A1* | 5/2015 | Chrystie | G01J 3/42 |
| | | | 374/161 |
| 2015/0209181 A1 | 7/2015 | Herekar et al. | |
| 2015/0373285 A1* | 12/2015 | Morris | G01J 3/28 |
| | | | 250/252.1 |
| 2016/0317833 A1 | 11/2016 | Tedford et al. | |
| 2017/0156597 A1* | 6/2017 | Whitehead | A61B 5/01 |

OTHER PUBLICATIONS

"thermoMETER CTVideo/CSVideo // Infrared temperature sensors," Micro-Epsilon, accessed at https://web.archive.org/web/20150417103509/http://www.micro-epsilon.com/download/products/dat-thermoMETER-CTVideo-CSVideo-en-us.pdf, archived on Apr. 17, 2015, accessed on Jun. 15, 2017, pp. 12.

International Search Report and Written Opinion for International Application No. PCT/US2017/058331 dated Jan. 9, 2018, pp. 10.

Berg, T.J.T.P.V.D., and Spekreijse, H., "Near Infrared Light Absorption in the Human Eye Media," Vision Research, vol. 37, No. 2, pp. 249-253 (1997).

Choi, T.Y., et al., "Thermal evaluation of laser exposures in an in vitro retinal model by microthermal sensing," Journal of Biomedical Optics, vol. 19, No. 9, pp. 097003-1-097003-4 (Sep. 2014).

Simanovskii, D., et al., "Cellular tolerance to pulsed heating," Proceedings of SPIE—Optical Interactions with Tissue and Cells XVI, vol. 5695, pp. 254-259 (Apr. 2005).

* cited by examiner

LASER DOSAGE DETERMINATION BY TEMPERATURE MONITORING

CROSS-REFERENCE

This patent application is section 371 nationalization of PCT Application No. PCT/US2017/058331 filed Oct. 25, 2017, which application is incorporated herein by specific reference in its entirety.

BACKGROUND

Unless otherwise indicated herein, the materials described herein are not prior art to the claims in the present application and are not admitted to be prior art by inclusion in this section.

Therapeutic radiation may be administered to an eye of a patient to treat various conditions of the eye that may negatively affect vision. It may be difficult to accurately measure an exposure level of the eye to the therapeutic radiation, which can damage the eye at excess exposure levels.

SUMMARY

Techniques described herein generally relate to laser dosage determination by temperature monitoring.

In an example embodiment, a laser-based ophthalmological surgical system includes a therapeutic radiation source, one or more optical elements, and a detector system. The therapeutic radiation source may be configured to emit therapeutic radiation. The one or more optical elements may be configured to direct the therapeutic radiation to a targeted area of an eye of a patient. A temperature of the targeted area may depend on a dosage of the therapeutic radiation. The detector system may be configured to measure thermal radiation emitted by the targeted area responsive to exposure to the therapeutic radiation. The one or more optical elements may be configured to optically couple the detector system to the targeted area.

In another example embodiment, a method to measure therapeutic radiation dosimetry may include irradiating a targeted area of an eye of a patient with therapeutic radiation. A temperature of the targeted area may depend on a dosage of the therapeutic radiation. The method may also include measuring thermal radiation emitted by the targeted area responsive to exposure to the therapeutic radiation to generate a measurement of the thermal radiation. The measurement of the thermal radiation may be indicative of the temperature of the targeted area and the dosage of the therapeutic radiation.

In some embodiments, a laser-based ophthalmological surgical system can include: a therapeutic radiation source configured to emit therapeutic radiation; one or more optical elements configured to direct the therapeutic radiation to a targeted area of an eye of a patient, wherein a temperature of the targeted area depends on a dosage of the therapeutic radiation; and a detector system configured to measure thermal radiation emitted by the targeted area responsive to exposure to the therapeutic radiation, wherein the detector system includes a first detector configured to detect radiation at a first wavelength and a second detector configured to detect radiation at a second wavelength shorter than the first wavelength, wherein the one or more optical elements are configured to optically couple the detector system to the targeted area. In some aspects, at least one of the first detector or second detector includes: a detector with a quantum efficiency, the detector configured to detect an intensity of the thermal radiation; and a processor device communicatively coupled to the detector and configured to receive the detected intensity from the detector, and calculate the temperature of the targeted area based on the detected intensity, the quantum efficiency of the detector, and a blackbody spectrum associated with a target temperature threshold of the targeted area. In some aspects, at least one of the first detector or second detector includes an infrared (IR) detector. In some aspects, at least one of the first detector or second detector comprises an infrared (IR) detector, wherein the IR detector includes an indium gallium sulfide (InGaS) IR detector, a mercury cadmium telluride (MCT) IR detector, or an indium phosphide (InP) IR detector. In some aspects, at least one of the first detector or second detector includes a bandwidth greater than 10 megahertz (MHz) and configured to measure the thermal radiation at sub microsecond temporal resolution.

In some embodiments, the one or more optical elements includes at least one filter positioned in an optical path between the targeted area and the detector system and wherein the filter is configured to block radiation with a wavelength less than one micrometer.

In some embodiments, the one or more optical elements includes at least one beam splitter. In some aspects, the at least one beam splitter is configured to provide the first wavelength to the first detector and provide the second wavelength to the second detector.

In some embodiments, the one or more optical elements includes a first filter positioned in a first optical path between the targeted area and the first detector, wherein the first filter is configured to pass radiation at the first wavelength to the first detector. Also, a second filter can be positioned in a second optical path between the targeted area and the second detector, wherein the second filter is configured to pass radiation at the second wavelength to the second detector. In some embodiments, a processor device can be communicatively coupled to the therapeutic radiation source and the detector system, wherein the processor device is configured to terminate exposure of the targeted area of the eye of the patient to the therapeutic radiation responsive to a measurement of the thermal radiation generated by the detector system meeting or exceeding a target temperature threshold.

In some embodiments, a method to measure therapeutic radiation dosimetry can include: irradiating a targeted area of an eye of a patient with therapeutic radiation, wherein a temperature of the targeted area depends on a dosage of the therapeutic radiation; and measuring thermal radiation emitted by the targeted area responsive to exposure to the therapeutic radiation to generate a measurement of the thermal radiation. In some aspects, the protocol for measuring thermal radiation can include: measuring thermal radiation in a first spectral band associated with a first temperature lower than a target temperature threshold to generate a first measurement of the thermal radiation; and measuring thermal radiation in a second spectral band associated with the target temperature threshold to generate a second measurement of the thermal radiation. In some aspects, a relationship between the first measurement and second measurement is indicative of the temperature of the targeted area and the dosage of the therapeutic radiation.

In some embodiments, the measuring of the thermal radiation to generate the measurement can include detecting an intensity of the thermal radiation to generate detected intensity, the method further comprising calculating the temperature of the targeted area based on the detected intensity, a quantum efficiency of at least one detector that generates the detected intensity, and a blackbody spectrum associated with a target temperature.

In some embodiments, the method can include filtering an optical path between the targeted area and a detector system that measures the thermal radiation to block radiation with wavelengths associated with temperatures less than a target temperature threshold.

In some embodiments, the method can include terminating exposure of the eye of the patient to the therapeutic radiation responsive to the measurement of the thermal radiation meeting or exceeding a target temperature threshold.

In some embodiments, irradiating the targeted area with the therapeutic radiation can include irradiating the targeted area with discrete pulses of the therapeutic radiation, wherein the discrete pulses of therapeutic radiation have different amounts of pulse energy.

In some embodiments, the method can include: determining a current dosage of the therapeutic radiation based on the first measurement responsive to the first measurement exceeding a first threshold and the second measurement being below a second threshold that is lower than the first threshold; determining a target dosage of the therapeutic radiation based on at least one of the current dosage, the first measurement, and the second measurement; and controlling the therapeutic radiation source to emit a discrete pulse with an amount of energy that corresponds to the target dosage. In some aspects, the method can include terminating exposure of the eye of the patient to the therapeutic radiation responsive to the therapeutic radiation source emitting a target dosage.

In some embodiments, the method can include synchronizing the measurement of the thermal radiation to discrete pulses of the therapeutic radiation.

In some embodiments, the measurement of thermal radiation comprises one or more measurements of the temperature of the targeted area, each of the one or more measurements is associated with a corresponding discrete pulse of the therapeutic radiation having a corresponding known amount of pulse energy. In some embodiments, the method can include: determining a target dosage of the therapeutic radiation based on the one or more measurements and the corresponding known amount of pulse energy; and controlling the therapeutic radiation source to emit a discrete pulse with an amount of pulse energy that corresponds to the target dosage.

In some embodiments, the method can include terminating exposure of the eye of the patient to the therapeutic radiation responsive to the therapeutic radiation source emitting the discrete pulse with the amount of pulse energy that corresponds to the target dosage.

In some embodiments, measuring the thermal radiation includes measuring the thermal radiation using at least one detector with a bandwidth greater than 10 megahertz (MHz) at sub microsecond temporal resolution.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information, as well as other features of this disclosure, will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings:

DETAILED DESCRIPTION

Figure 1A:
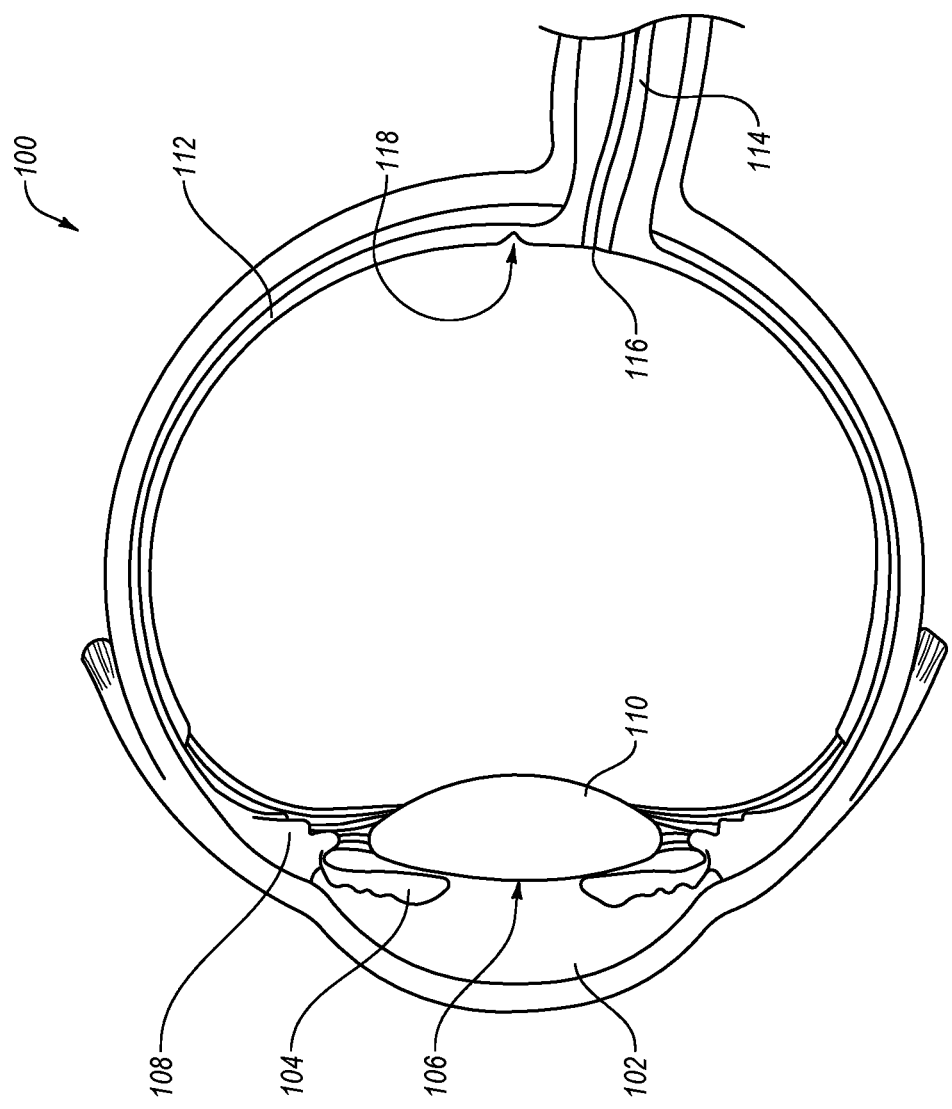
FIG. 1A is a cross-sectional view of an example human eye (hereinafter "eye")

This disclosure is generally drawn to methods, apparatus, systems, devices, and computer program products related to laser dosage determination by temperature monitoring.

In this detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. The aspects of the present disclosure, as generally described herein, and illustrated in the Figures, can be arranged, substituted, combined, separated, and designed in a wide variety of different configurations, all of which are explicitly contemplated herein.

FIG. 1A is a cross-sectional view of an example human eye (hereinafter "eye") 100, arranged in accordance with at least one embodiment described herein. The eye 100 may include a cornea 102, an iris 104, a pupil 106, a ciliary body 108, a lens 110, a retina 112, and an optic nerve 114. The retina 112 generally includes a light-sensitive layer of tissue upon which optics of the eye 100 project an image of the visual world external to the eye 100. Through a series of chemical and electrical events, nerve impulses may be triggered in response to light striking the retina 112. The nerve impulses may be processed in vision centers of the brain such that the visual world may be perceived by a person.

As illustrated in FIG. 1A, the retina 112 includes an optic disc 116, sometimes referred to as the "blind spot", and a macula 118 temporal to the optic disc 116.

Figure 1B:
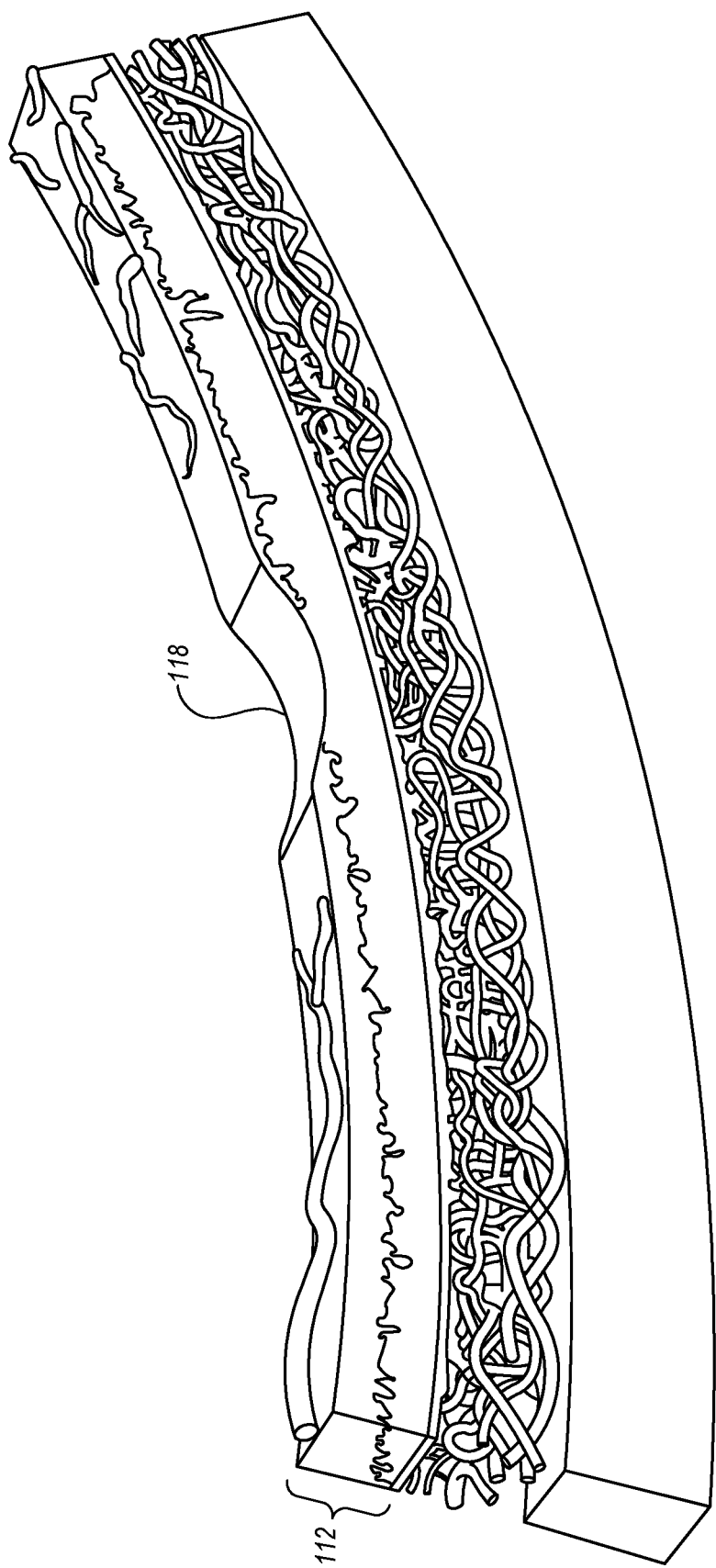
FIG. 1B is a cross-sectional perspective view of a portion of a retina and macula of FIG. 1B.

FIG. 1B is a cross-sectional perspective view of a portion of the retina 112 and the macula 118 of FIG. 1A, arranged in accordance with at least one embodiment described herein.

Figure 1C:
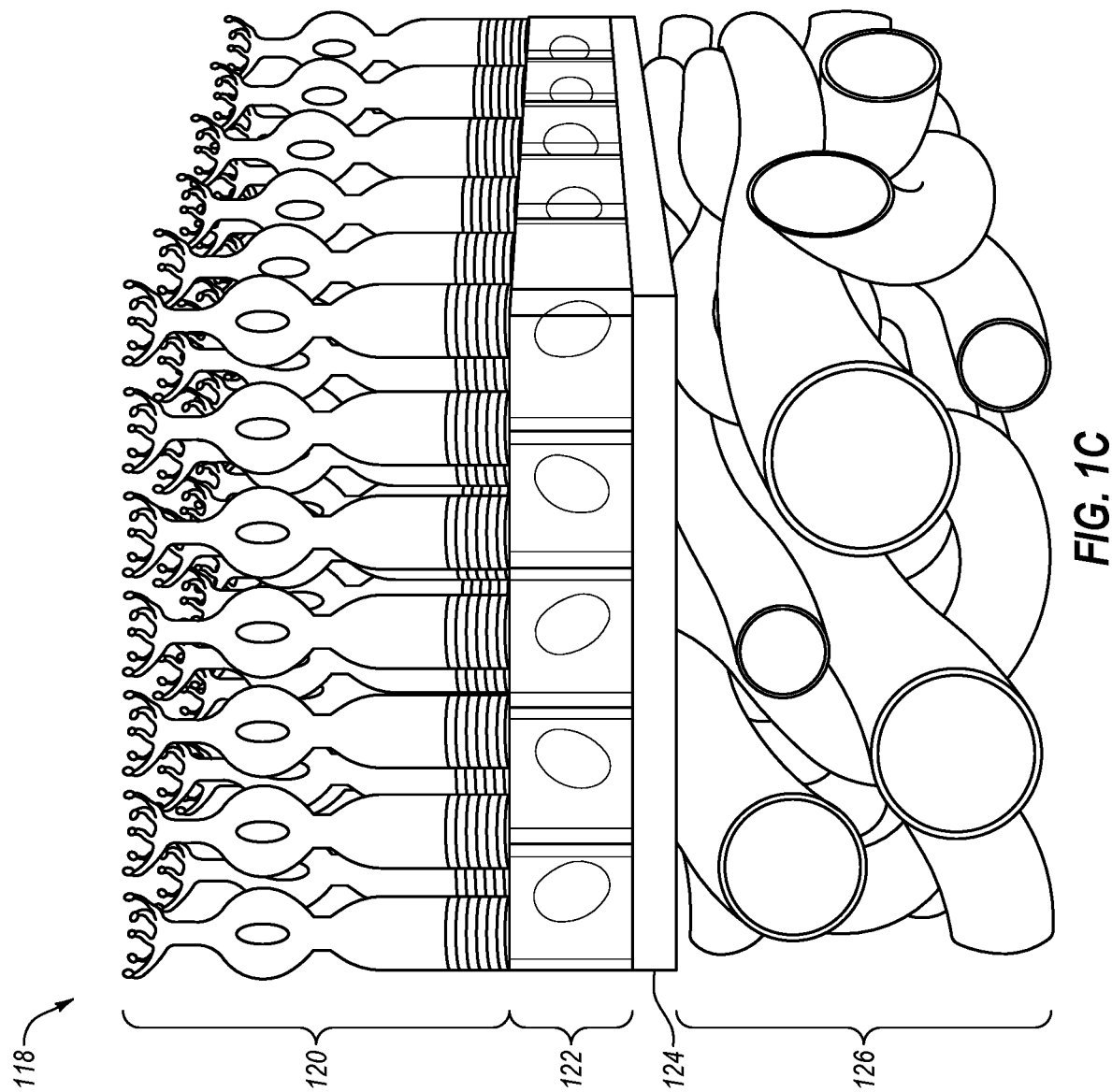
FIG. 1C is a cross-sectional perspective view of a portion of the macula of FIG. 1B.

FIG. 1C is a cross-sectional perspective view of a portion of the macula 118 of FIG. 1B, arranged in accordance with at least one embodiment described herein. FIG. 1C depicts various layers that may make up the macula 118, including photoreceptors 120, retinal pigment epithelial (RPE) cells 122, Bruch's membrane 124, and choroid 126. The macula 118 may have a relatively high concentration of photoreceptors 120 compared to the rest of the retina 112 and without blood vessels, for central and/or high resolution vision. The RPE cells 122 may nourish the photoreceptors 120 by supplying nutrients from the choroid 126 and transporting extracellular material out through the Bruch's membrane 124.

Various conditions may adversely affect vision in the eye 100. For instance, with reference to FIGS. 1A-1C, age-related macular degeneration (AMD) may involve degradation of the RPE cells 122 in the macula 118. In dry AMD, degraded RPE cells 122 may fail to transport extracellular material which may then begin to build up ("Drusen") in between the Bruch's membrane 124 and the RPE cells 122. The Drusen may interfere with the supply of nutrients to the photoreceptors 120, which can lead to vision loss. In wet AMD, new blood vessels (neovascularization) may grow from the choroid 126 and penetrate the Bruch's membrane 124 and the RPE cells 122 to supply nutrients to the photoreceptors 120. The new blood vessels may be weak and prone to bleeding and leakage, which may result in blood and protein leakages, which in turn may damage the photoreceptors 120 and fuel rapid vision loss.

Another condition that may adversely affect vision in the eye 100 may be diabetic macular edema (DME). In more detail, persons with diabetes may experience a slowing of metabolism over time, which may reduce the ability of retinal vessels to deliver enough nutrients, which in turn may induce neovascularization. Fluid leakage from the neovascularization may cause the retina 112 to swell, causing vision loss.

Another condition that may adversely affect vision in the eye 100 may be central serous chorioretinopathy (CSC). In CSC, leakage of fluid accumulates under the central macula 118, resulting in blurred or distorted vision which may progressively decline with each recurrence.

Some embodiments described herein include a laser-based ophthalmological surgical system that includes a therapeutic radiation source configured to emit therapeutic radiation to treat AMD, DME, CSC, and/or other conditions of the eye 100. In general, the therapeutic radiation may be absorbed by RPE cells 122 targeted with the therapeutic radiation. Specifically, the therapeutic radiation may be absorbed by melanin or other chromophore in the RPE cells 122. The absorbed therapeutic radiation may be converted to heat, which may lead to formation of microbubbles in the RPE cells 122. The microbubbles may burst or otherwise destroy RPE cells 122. By targeting degraded RPE cells included in the RPE cells 122, the degraded RPE cells can be destroyed to prevent them from causing further damage.

According to some embodiments, such laser-based ophthalmological surgical systems may use real-time feedback to detect RPE damage and stop therapeutic radiation automatically based on the feedback prior to excessively damaging the targeted RPE cells 122. In an example embodiment, the therapeutic radiation may be administered to the targeted RPE cells 122 in pulses that may have an energy per pulse (hereinafter "pulse energy") that may vary from one pulse to the next. The administration of pulses may be terminated in response to the feedback indicating a maximum, or at least target, exposure to the therapeutic radiation.

The therapeutic radiation may, in some embodiments, be generally more effective at treating conditions of the eye at higher exposure levels. However, at a particular level of exposure, e.g., pulse energy, to the therapeutic radiation, therapeutic radiation may cause excessive damage to the eye that may result in vision loss. To avoid or reduce the likelihood of vision loss due to excessive exposure to the therapeutic radiation while permitting exposure up to a sufficiently high level to be effective, some embodiments described herein may start administration of the therapeutic radiation at a relatively low exposure that ramps up with each successive pulse until real-time feedback indicates a threshold exposure has been reached. In an example, the first pulse of therapeutic radiation may be at about 50% of a relatively high energy level, such as a maximum energy level. More generally, the first pulse may be at a relatively low energy level, and each successively administered pulse of therapeutic radiation may be increased compared to the preceding pulse. The amount of increase from pulse to pulse may be fixed or variable. For instance, in an example embodiment, the amount of increase from pulse to pulse may be fixed at 5% of the relatively high energy level.

In another example, a relatively small number of successive pulses, such as two, may be administered, each with relatively low but different pulse energy. Real-time feedback for each of the relatively small number of successive pulses may be used to calculate or otherwise determine a particular pulse energy that will result in the maximum, or at least target, exposure to the therapeutic radiation. In this and other embodiments, rather than ramping up the pulse energy by the fixed amount over a series of successive pulses, the therapeutic radiation may be increased from the pulse energy for the last one of the relatively small number of successive pulses directly to the particular pulse energy that will result in the maximum, or at least target, exposure to the therapeutic radiation. Such an approach may reduce a total amount of treatment time.

In these and other embodiments, the real-time feedback may measure exposure of the targeted RPE cells to the therapeutic radiation by measuring the formation and/or bursting of microbubbles that form on melanosomes of the targeted RPE cells in response to exposure to the therapeutic radiation, and/or by measuring thermal radiation emitted by the targeted RPE cells responsive to absorbing the therapeutic radiation. In an example embodiment, the formation and/or bursting of the microbubbles may be measured with optical feedback and/or acoustic feedback. In particular, the targeted RPE cells may reflect and/or emit optical and/or acoustic signals that may vary depending on the presence, absence, and/or characteristics (e.g., size, velocity) of the microbubbles. Excessive exposure to the therapeutic radiation after microbubble formation and RPE damage could damage other retinal structures, which may lead to formation of scotoma on the retina.

Figure 2:
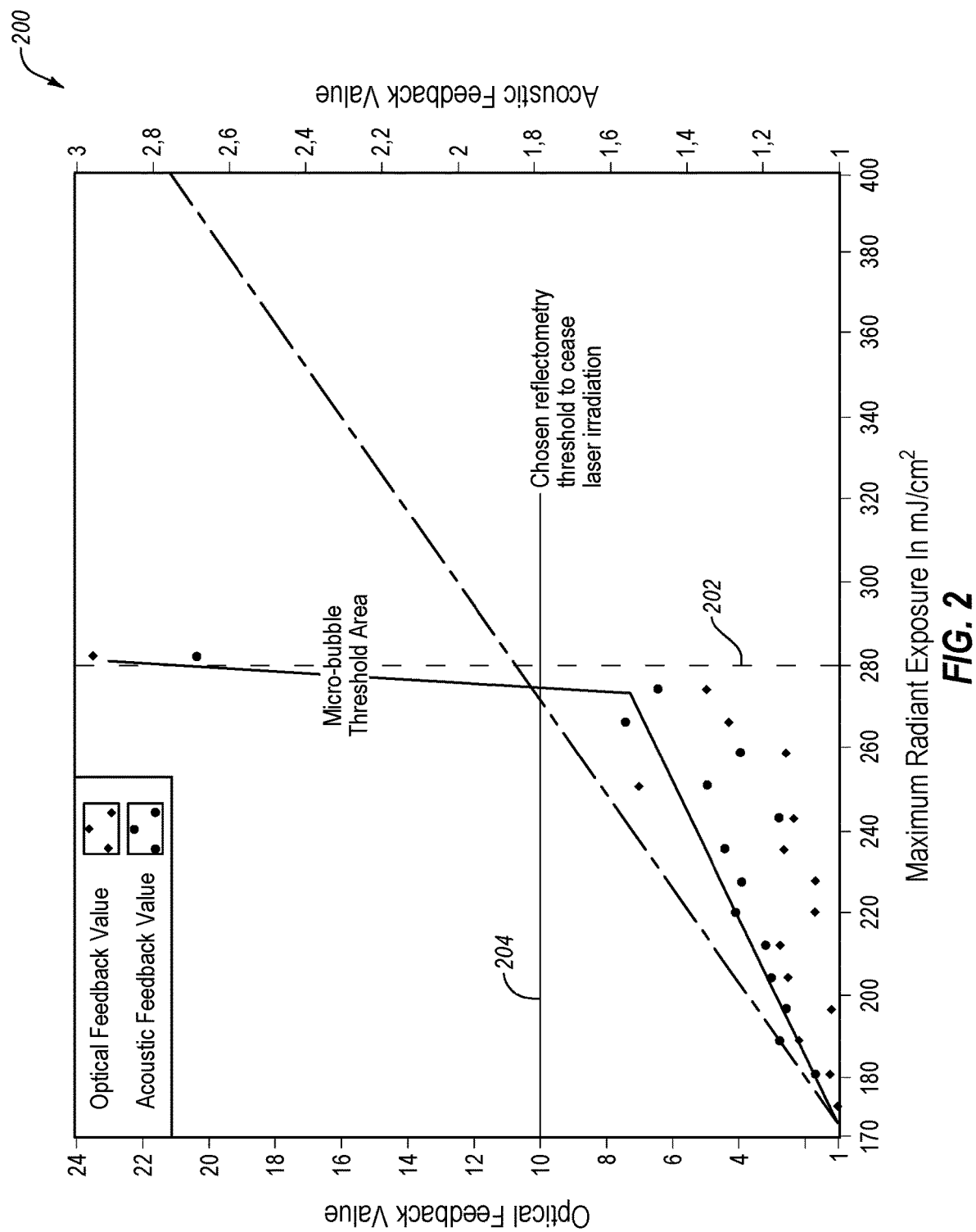
FIG. 2 is a graphical representation of an example feedback response to therapeutic radiation that may be generated by a laser-based ophthalmological surgical system.

FIG. 2 is a graphical representation 200 of an example feedback response to therapeutic radiation that may be generated by a laser-based ophthalmological surgical system, arranged in accordance with at least one embodiment described herein. The horizontal axis is radiant exposure to the therapeutic radiation in millijoules per square centimeter (mJ/cm2), the left vertical axis is optical feedback value in microwatts, and the right axis is acoustic feedback value in volts. FIG. 2 includes data points representing the measured optical feedback (diamonds in FIG. 2) and acoustic feedback (circles in FIG. 2) as a function of therapeutic radiation exposure level. Each data point may represent a measurement of the optical or acoustic feedback from the targeted RPE cells and/or from microbubbles thereon after exposure to a pulse of the therapeutic radiation at a corresponding exposure level. All of the optical feedback data points may be collectively referred to as an optical signal and all of the acoustic feedback data points may be collectively referred to as an acoustic signal.

FIG. 2 additionally includes a vertical reference zone 202, at around 280 mJ/cm2 in the example of FIG. 2, that represents a microbubble threshold area at a therapeutic radiation exposure level that may be known or expected to cause excessive damage to the targeted RPE cells. FIG. 2 additionally includes a horizontal reference line 204 at a threshold optical feedback value, at 10 arbitrary units (a.u.) in the example of FIG. 2, which may be selected as an optical feedback value after which irradiation with the therapeutic radiation may be terminated to avoid or reduce the likelihood of excessive damage to the targeted RPE cells.

The optical signal in the example of FIG. 2 may be generated by measuring reflected therapeutic radiation or other reflected radiation from the targeted RPE cells and/or from microbubbles that form thereon.

The acoustic signal in the example of FIG. 2 may be generated by measuring the acoustic response of the targeted RPE cells and/or the microbubbles that form thereon.

As illustrated in FIG. 2, the optical signal and the acoustic signal in this example may both be somewhat noisy and may exhibit substantial fluctuations, particularly around the vertical reference zone 202. This strong fluctuation in the optical signal and the acoustic signal may impose a difficulty in accurately determining when the optical signal and the acoustic signal is at or near a corresponding threshold feedback value indicative of a therapeutic radiation threshold exposure level.

Embodiments described herein may alternatively or additionally measure thermal radiation emitted by the targeted RPE cells exposed to the therapeutic radiation. The thermal radiation may be emitted by the targeted RPE cells responsive to absorption by the targeted RPE cells of some or all of the therapeutic radiation. The measured thermal radiation may be used as the real-time feedback to measure exposure of the targeted RPE cells to the therapeutic radiation. In these and other embodiments, the thermal radiation may be less dependent on bubble dynamics (e.g., formation and/or bursting) of the microbubbles than the optical and/or acoustic signals of FIG. 2. Alternatively or additionally, the targeted RPE cells may absorb the thermal radiation, which may then be converted to heat in proportion to the thermal radiation exposure level. As such, measuring the thermal radiation emitted by the targeted RPE cells may provide a more direct measure of the thermal radiation exposure level than the optical and/or acoustic signals of FIG. 2.

In these and other embodiments, the measured thermal radiation may be less noisy and/or may have fewer fluctuations than the optical and/or acoustic signals of FIG. 2. Accordingly, one or more measurements of thermal radiation emitted by the targeted RPE cells may be used as the real-time feedback instead of or in addition to one or both of the optical signal or the acoustic signal of FIG. 2. The one or more measurements may include an intensity of the thermal radiation and/or a temperature of the targeted RPE cells derived from the intensity.

In this and other embodiments, a laser-based ophthalmological surgical system may include a therapeutic radiation source, one or more optical elements, and a detector system. The therapeutic radiation source may be configured to emit therapeutic radiation. The one or more optical elements may be configured to direct the therapeutic radiation to one or more targeted RPE cells included in a targeted area of an eye of a patient. A temperature of the targeted area and/or of the targeted RPE cells may depend on a dosage of the therapeutic radiation, or exposure level of the targeted area to the therapeutic radiation. The detector system may be configured to measure thermal radiation emitted by the targeted area responsive to exposure to the therapeutic radiation and may include, e.g., an infrared (IR) detector. The one or more optical elements may be configured to optically couple the detector system to the targeted area. Various detection approaches may be implemented, some of which are described in more detail elsewhere herein.

In some embodiments, a temperature at which excess damage may occur to an eye of a patient in response to exposure to therapeutic radiation may be known and/or estimated. This temperature may be referred to as a damage temperature threshold. The damage temperature threshold may be known and/or estimated based on experimental results and/or simulations that may demonstrate a temperature at and/or above which the RPE cells in the targeted area and/or other portions of the eye of the patient are subjected to excessive damage, e.g., in the form of scotoma formation.

A target temperature threshold may be selected to be equal to or less than the damage temperature threshold. In some embodiments, the target temperature threshold may be in a range from 340-360 Kelvin (K) or in a range from 350-355 K. Alternatively or additionally, the targeted area of the eye of the patient may be exposed to the therapeutic radiation until and/or such that measured thermal radiation indicates the targeted area has reached the target temperature threshold. The target temperature threshold may be selected to be less than the damage temperature threshold to provide some margin for error. Alternatively, the target temperature threshold may be selected to be equal to the damage temperature threshold. In these and other embodiments, the targeted area may be assumed to be and/or may be approximated as a black body and thermal radiation emitted by the targeted area responsive to exposure to the therapeutic radiation may be measured to determine the temperature of the targeted area, as described in more detail elsewhere.

Figure 3A:
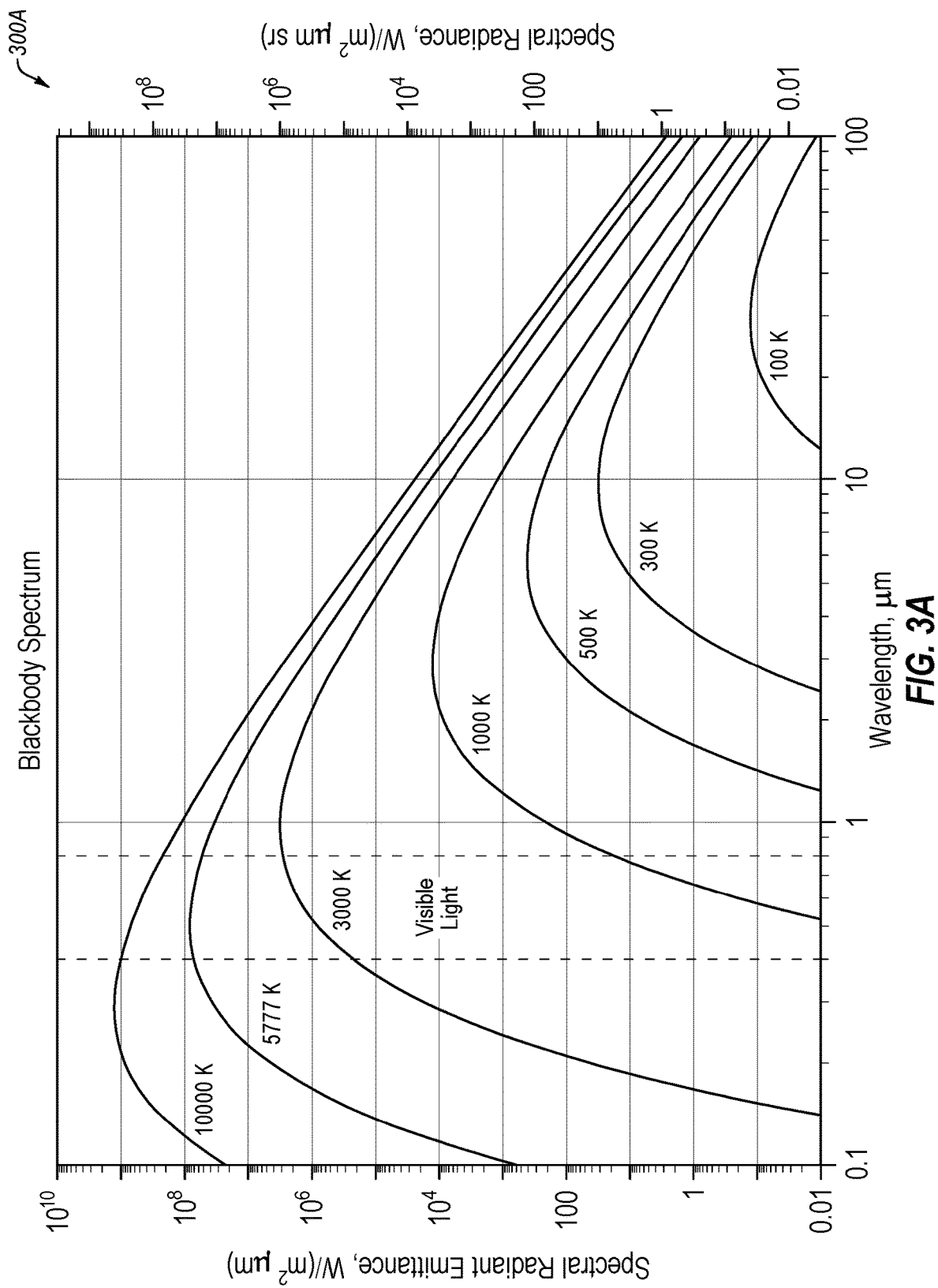
FIGS. 3A and 3B are graphical representations of various blackbody spectra at different temperatures.
Figure 3B:
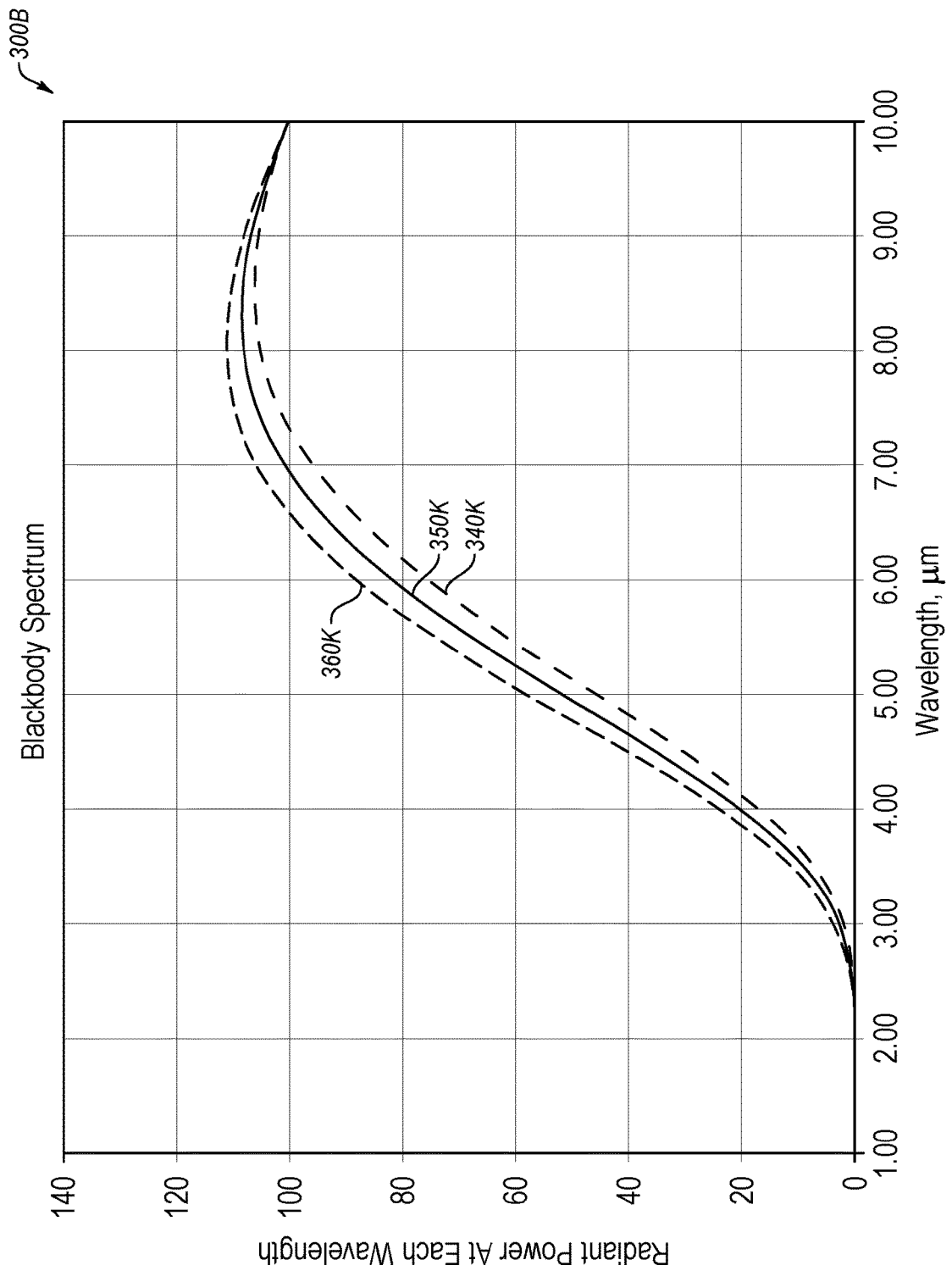

FIGS. 3A and 3B are graphical representations 300A and 300B of various blackbody spectra at different temperatures, arranged in accordance with at least one embodiment described herein. In FIG. 3A, each blackbody spectrum is labeled with a temperature in Kelvin (K) at which the blackbody spectrum may be emitted by a black body. The horizontal axis and the vertical axis in FIG. 3A both have a logarithmic scale. The horizontal axis is wavelength in micrometers (μm), and the left and right vertical axes are, in effect, thermal radiation intensity. More specifically, the left vertical axis is spectral radiant emittance in W/(m2 μm) and the right vertical axis is spectral radiance in W/(m2 μm sr). Thus, FIG. 3A illustrates various blackbody spectra at different temperatures in terms of thermal radiation intensity as a function of wavelength.

It can be inferred from FIG. 3A, in particular at least from the black body spectrum at 300 K and the black body spectrum at 500 K, that a black body at a temperature in a range from 300-380 K may have a blackbody spectrum with at least some spectral components at wavelengths of about 2 μm or less, with the intensity at any given spectral component in this range increasing with increasing temperature. For instance, the intensity of the blackbody spectra at a wavelength of 2 µm may be greater at 350 K than at 300 K, and still greater at 380 K. A graph (such as the graph of FIG. 3A), table, equation, or other information may relate thermal radiation intensities, wavelengths, and/or temperatures of black bodies such that one or more of the foregoing parameters may be calculated, estimated, or otherwise determined when one or more others of the foregoing parameters are known. Thus, the thermal radiation intensity at a given wavelength, when measured, may be used to determine a temperature of a black body. Alternatively or additionally, the thermal radiation intensities at two or more different wavelengths, a ratio thereof, or some other relationship therebetween, may be used to determine the temperature of the black body.

The targeted area in the eye of the patient may be assumed to be and/or may be approximated as a black body. As such, the thermal radiation emitted by the targeted area may be measured and used to determine the temperature of the targeted area, which in turn may be used to determine the therapeutic radiation dosage of the targeted area. For instance, the temperature of and thus the thermal radiation emitted by the targeted area may be directly proportional to and/or may have some other relationship to the therapeutic radiation dosage.

The temperature range 300-380 K may be and/or may include a range of temperatures that the targeted area of the eye may be expected to reach responsive to an expected range of therapeutic radiation dosages. Because the blackbody spectra associated with the temperature range from 300-380 K may each have at least some spectral components at wavelengths of about 2 µm or less, some embodiments described herein may be implemented with detector systems and/or optical components that are suitable for wavelengths of about 2 µm or less. Some laser-based ophthalmological surgical systems may already include and/or may already be designed with detector systems and/or optical components suitable for such wavelengths such that implementing one or more embodiments described herein in such laser-based ophthalmological surgical systems may be relatively simple and straightforward with relatively few modifications.

In FIG. 3B, each blackbody spectrum is labeled with a temperature in Kelvin (K) at which the blackbody spectrum may be emitted by a black body, with three spectra at, respectively, 340 K, 350 K, and 360 K. The horizontal axis and the vertical axis in FIG. 3B both have a linear scale. The horizontal axis is wavelength in µm and the left vertical axis is, in effect, thermal radiation intensity. More specifically, the left vertical axis is radiant power. Thus, FIG. 3B illustrates various blackbody spectra at different temperatures in terms of thermal radiation intensity as a function of wavelength.

Based on the spectra of FIG. 3B, measurements of thermal radiation for blackbody spectra in the range of 340-360 K at a wavelength of about 2 µm or less may be difficult. Accordingly, some embodiments may measure blackbody spectra in the range of 340-360 K at higher wavelengths than 2 µm or less, such as at least 3 µm, or at least 4 µm. In an example implementation, some embodiments may measure blackbody spectra at 4 µm or 5 µm.

In particular, some embodiments described herein may be implemented with detector systems and/or optical components that are suitable for wavelengths of about 4 and/or 5 µm. For each of the 340 K, 350 K, and 360 K spectra in FIG. 3B, it can be seen that the thermal radiation intensity is much greater at 4 and 5 µm than at 2 µm.

In some embodiments, the thermal radiation intensity may be detected at both 4 and 5 µm and the ratio of the two measurements may be used to determine the temperature and thus the thermal radiation exposure at the eye of the patient. For instance, the ratio of the thermal radiation measured at 4 µm to the thermal radiation measured at 5 µm for the 360 K blackbody spectrum is about 2.41803. The same ratio for the 350 K blackbody spectrum is about 2.55996 and for the 340 K blackbody spectrum is about 2.71936. This ratio monotonically decreases as temperature increases near an example target temperature threshold of 353 K. Accordingly, by measuring the thermal radiation intensity at both 4 and 5 µm, and determining the ratio of the two, the temperature and thus the thermal radiation exposure at the eye of the patient may be determined in some embodiments.

Figure 4:
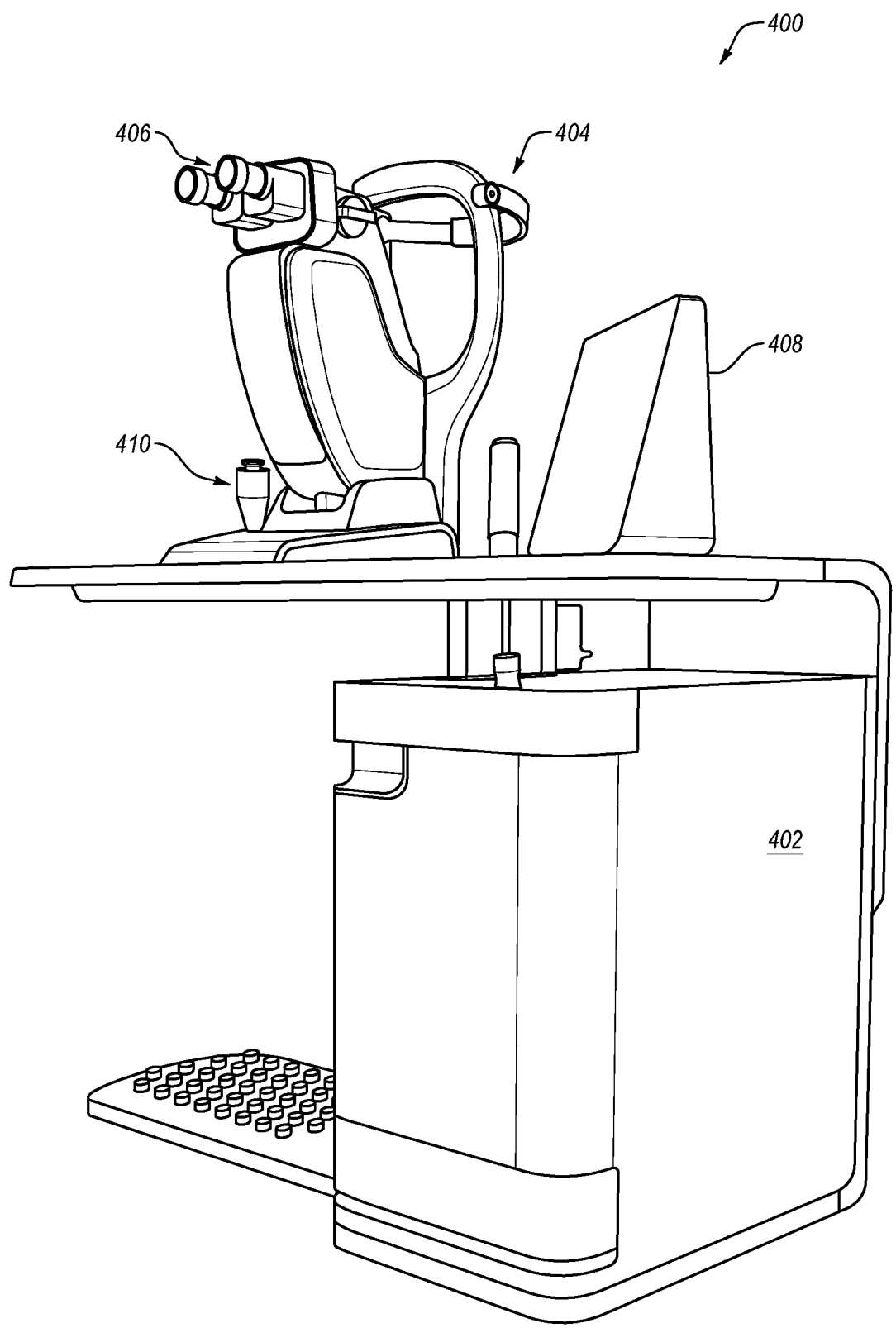
FIG. 4 is a perspective view of an example laser-based ophthalmological surgical system in which thermal radiation detection may be implemented.

FIG. 4 is a perspective view of an example laser-based ophthalmological surgical system (hereinafter "system") 400 in which thermal radiation detection may be implemented, arranged in accordance with at least one embodiment described herein. As illustrated, the system 400 may include one or more of a console 402, a head fixation assembly 404, a microscope 406, a graphical user interface (GUI) 408, and one or more input devices 410.

The console 402 may include a therapeutic radiation source configured to emit therapeutic radiation. The console 402 may also include one or more control systems (e.g., one or more processors, drivers, or other circuits), a cooling system, or other systems or components. Additional details regarding an example therapeutic radiation source are described elsewhere herein.

The therapeutic radiation may be directed by one or more optical elements of the system 400 from the therapeutic radiation source in the console 402 into an eye of a patient during treatment of the eye of the patient with the system 400. The one or more optical elements may be included in one or more of the console 402, the microscope 406, and/or other components of the system 400 and/or may be provided as discrete components within the system 400.

The head fixation assembly 404 may be configured to position and retain a head of the patient during treatment of the eye of the patient with the therapeutic radiation. For instance, the head fixation assembly 404 may be configured to position and retain the head of the patient with the eye of the patient aligned to receive the therapeutic radiation.

The microscope 406 may be used by a treatment provider to observe the patient's eye during treatment. Alternatively or additionally, the microscope 406 or other component of the system 400 may include a targeting radiation source that may be optically aligned to target a same location as the therapeutic radiation. The targeting radiation source may emit targeting radiation to identify a specific location within the patient's eye currently targeted to receive therapeutic radiation. In this and other embodiments, the treatment provider may operate the input device 410, the GUI 408, and/or other elements of the system 400 to adjust the particular location within the patient's eye that is targeted by the targeting radiation and/or the therapeutic radiation.

Figure 5A:
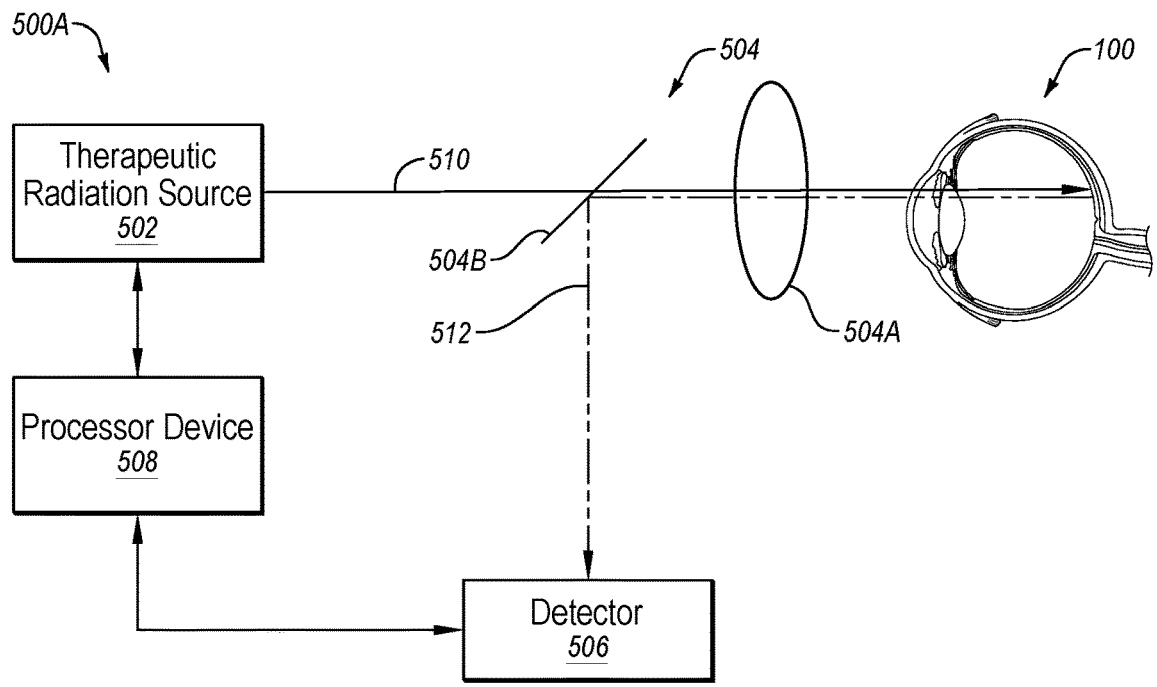
FIG. 5A is a block diagram of an example laser-based ophthalmological surgical system.

FIG. 5A is a block diagram of an example laser-based ophthalmological surgical system (hereinafter "system") 500A, arranged in accordance with at least one embodiment described herein. The system 500A may include or correspond to the system 400 of FIG. 4. The system 500A may include a therapeutic radiation source 502, one or more optical elements 504, and a detector 506. Alternatively or additionally, the system 500A may include a processor device 508. The detector 506 and the processor device 508 combined may form a detector system. The system 500A may include one or more other elements not depicted in FIG. 5A for simplicity.

The therapeutic radiation source 502 may be configured to emit therapeutic radiation 510 with a center wavelength. For instance, the therapeutic radiation 510 may have a center wavelength in a range from 440-500 nanometers (nm), or in a range from 520 nm to about 540 nm, such as 527 nm, or in a range from 575 nm or higher, such as 577 nm, or in some other range. The therapeutic radiation 510 in some embodiments may be pulsed, meaning the therapeutic radiation source 502 may emit the therapeutic radiation 510 as discrete pulses. The pulses of therapeutic radiation 510 may each have a pulse duration in a range from 1.6 microseconds to 1.8 microseconds, and may be administered periodically in some embodiments, with a pulse frequency in a range of 50 hertz (Hz) to 200 Hz or higher (e.g., 500 Hz), such as 100 Hz. As used herein, "pulse frequency" may refer to a frequency at which the discrete pulses of therapeutic radiation 510 are emitted by the therapeutic radiation source 502, e.g., a repetition rate of the discrete pulses of therapeutic radiation 510. The pulses of therapeutic radiation 510 may be substantially flat-topped or may have some other shape.

In some embodiments, the therapeutic radiation 510 emitted by the therapeutic radiation source 502 may have up to a maximum energy of at least 0.4 millijoules (mJ). The therapeutic radiation source 502 may be controlled to emit discrete pulses of the therapeutic radiation 510 that have a pulse energy in a range between 0 mJ up to the maximum energy. For instance, the discrete pulses of therapeutic radiation 510 may be sequentially ramped up beginning at a relatively low pulse energy (e.g., 50% of the maximum energy) and successively ramping up in pulse energy by a fixed or variable amount (e.g., 5% of the maximum energy) until optical feedback, acoustic feedback, or thermal radiation feedback indicates a threshold exposure level of the eye 100 to the therapeutic radiation 510 has been reached. Alternatively, successive discrete pulses may have their pulse energy changed from one pulse to the next according to some other scheme.

The optical elements 504 may be configured to direct the therapeutic radiation 510 to the targeted area of the eye 100, and in particular to targeted RPE cells within the targeted area. A temperature of the targeted area of the eye 100 may depend on the dosage, or pulse energy, of the therapeutic radiation 510. The optical elements 504 may additionally be configured to optically couple the detector 506 to the targeted area of the eye 100 such that the detector 506 may receive and measure thermal radiation 512 emitted by the targeted area responsive to exposure to the therapeutic radiation.

The optical elements 504 in FIG. 5A include a microscope objective lens 504A (hereinafter "lens 504A") and a beam splitter 504B. In FIG. 5A, the lens 504A and the beam splitter 504B are both common to optical paths of the therapeutic radiation 510 and the thermal radiation 512. Alternatively or additionally, the optical elements 504 may include other components not illustrated in FIG. 5A, some of which may be common to both optical paths, others of which may be in the optical path of the therapeutic radiation 510 but not in the optical path of the thermal radiation 512, and/or others of which may be in the optical path of the thermal radiation 512 but not in the optical path of the therapeutic radiation 510.

The lens 504A may be configured to collect the thermal radiation 512 emitted from the eye 100 responsive to exposure to the therapeutic radiation 510. The lens 504A may be included in, e.g., the microscope 406 of FIG. 4.

The beam splitter 504B may be configured to pass the thermal radiation 512 from the therapeutic radiation source 502 to the eye 100. The beam splitter 504B may also be configured to redirect the thermal radiation 512 collected from the eye 100 toward the detector 506.

In an example, the beam splitter 504B may include a dichroic beam splitter with a cutoff wavelength of 1 μm such that radiation incident on the beam splitter 504B with a wavelength of at least 1 μm may be redirected to the detector 506. In this and other embodiments, the beam splitter 504B may function as a filter insofar as it may effectively block radiation with wavelengths less than 1 μm from being directed to the detector 506.

The detector 506 may have a quantum efficiency which may be associated with a particular wavelength or wavelength range. In at least one embodiment, the detector 506 may be configured detect radiation with wavelengths up to 2 μm. In other embodiments, the detector 506 may be configured to detect radiation with wavelengths greater than 2 μm, such as radiation with wavelengths of 3 μm, 4 μm, 5 μm, and/or other wavelengths. The detector 506 may be configured to receive the thermal radiation 512 and detect its intensity or other parameter as a measure of the thermal radiation 512. Alternatively or additionally, the detector 506 may include an IR detector, such as an indium gallium sulfide (InGaS) IR detector, a mercury cadmium telluride (MCT) IR detector, or an indium phosphide (InP) IR detector. In at least one embodiment, the detector 506 may have a bandwidth greater than 10 megahertz (MHz) and may be configured to measure the thermal radiation 512 at sub microsecond temporal resolution.

The processor device 508 may be communicatively coupled to the detector 506 and/or to the therapeutic radiation source 502. The processor device 508 may be configured to receive the detected intensity from the detector 506. Alternatively or additionally, the processor device 508 may be configured to calculate the temperature of the targeted area of the eye 100 based on the detected intensity, the quantum efficiency of the detector, and a blackbody spectrum. The blackbody spectrum may be associated with the target temperature threshold. Alternatively or additionally, the blackbody spectrum may include one or more of the blackbody spectra of FIG. 3A, or one or more similar blackbody spectra at different temperatures than those of FIG. 3A.

In an example embodiment, the processor device 508 may control the therapeutic radiation source 502 to emit discrete pulses of the therapeutic radiation 510 at a particular pulse frequency, pulse duration, and/or pulse energy. For instance, the therapeutic radiation source 502 may be controlled to emit a first discrete pulse with a first pulse energy and a second discrete pulse with a second pulse energy. The detector 506 may detect the intensity of the thermal radiation 512 emitted from the eye 100 after exposure of the eye 100 to each of the first and second discrete pulses. The processor device 508 may determine, based on the detected intensities, a first temperature of the eye 100 responsive to exposure to the first discrete pulse with the first pulse energy and a second temperature of the eye 100 responsive to exposure to the second discrete pulse with the second pulse energy. From the foregoing, the processor device 508 may then determine a third pulse energy for a third discrete pulse of the therapeutic radiation 510 that may cause the eye 100 to reach a third temperature, such as the target temperature threshold, and may control the therapeutic radiation source 502 to emit the third discrete pulse with the third pulse energy.

Alternatively or additionally, the beam splitter 504B and/or another filter included in the optical elements 504 and in an optical path between the eye 100 and the detector 506 may be configured to block wavelengths associated with temperatures less than the target temperature threshold. For instance, referring to FIG. 3A, if the target temperature threshold is in the range 350-355 K, such as 353 K, the filter may be configured to block relatively longer wavelengths associated with blackbody spectra at temperatures less than 353 K or other suitable target temperature threshold. In such embodiments, the therapeutic radiation 510 may be determined to be at or in excess of a target therapeutic radiation exposure level responsive to the detected intensity of the thermal radiation 512 being at or in excess of a detection threshold.

Figure 5B:
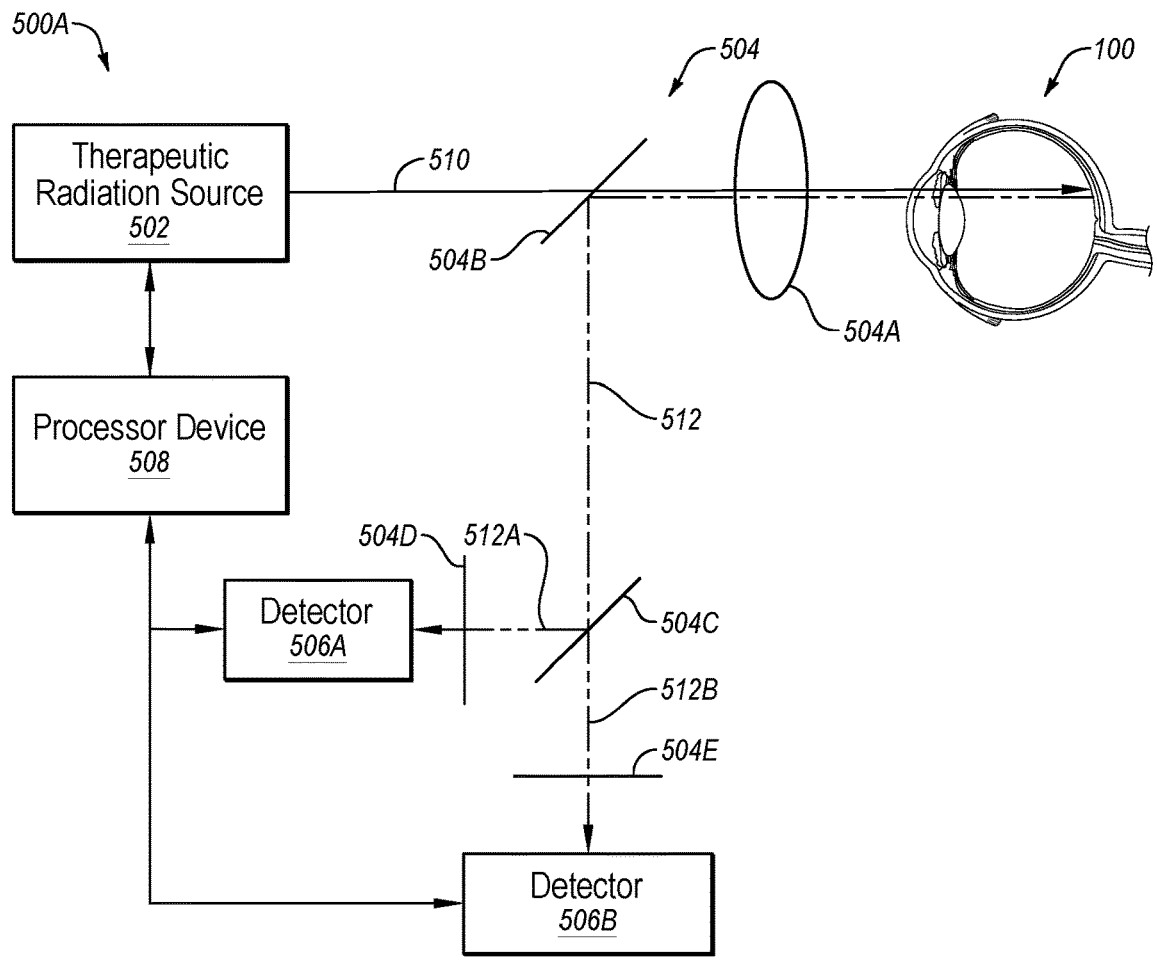
FIG. 5B is a block diagram of another example laser-based ophthalmological surgical system.

FIG. 5B is a block diagram of another example laser-based ophthalmological surgical system (hereinafter "system") 500B, arranged in accordance with at least one embodiment described herein. The system 500B may include or correspond to the system 400 of FIG. 4. The system 500B may be similar in some respects to the system 500A of FIG. 5A and may include the same or similar components. For instance, the system 500B may include the therapeutic radiation source 502, one or more optical elements 504, a first detector 506A, a second detector 506B, and the processor device 508.

The first and second detectors 506A, 506B may be the same or similar to the detector 506 of FIG. 5A. Alternatively or additionally, the first detector 506A may be configured to detect radiation, e.g., thermal radiation 512, at a first wavelength while the second detector 506B may be configured to detect radiation at a second wavelength different than the first wavelength. Additional aspects of the first and second detectors 506A, 506B according to at least one embodiment are described below.

The one or more optical elements 504 of FIG. 5B may include the lens 504A and the beam splitter 504B of FIG. 5A and may additionally include other components, such as a second beam splitter 504C, a first bandpass filter 504D, and a second bandpass filter 504E.

The second beam splitter 504C may generally be configured to split the thermal radiation 512 such that a first portion 512A of the thermal radiation 512 may be directed toward the first detector 506A and a second portion 512B of the thermal radiation 512 may be directed toward the second detector 506B. In this and other embodiments, the second beam splitter 504C may include a 50/50 beam splitter or other suitable beam splitter.

Each of the first and second bandpass filters 504D, 504E may have a center wavelength and a bandwidth, where the center wavelengths of the first and second bandpass filters 504D, 504E may be different from each other. The bandwidths of the first and second bandpass filters 504D, 504E may be the same or different. In an example, each of the first and second bandpass filters 504D, 504E may have a 10 nm bandwidth. The center wavelengths of the first and second bandpass filters 504D, 504E may both be in a range from, e.g., 1 to 2 µm, but may be offset from each other, e.g., by 50 nm or more. For instance, the center wavelength of the first bandpass filter 504D may be 1.15 µm (or 1150 nm), while the center wavelength of the second bandpass filter 504E may be 1.10 µm (or 1100 nm).

The inclusion of the first and second bandpass filters 504D, 504E in the optical elements 504 may configure the first and second detectors 506A, 506B to detect different spectral components of the thermal radiation 512. Such an arrangement may provide a more accurate determination of blackbody radiation and/or temperature of the eye 100 responsive to exposure to the therapeutic radiation 510. For instance, the discrete pulses of therapeutic radiation 510 may be administered beginning at a relatively low pulse energy that increases from one discrete pulse to the next. Where the first bandpass filter 504D has a higher center wavelength (e.g., 1.15 µm) than the second bandpass filter 504E (e.g., 1.10 µm), the first detector 506A may detect the thermal radiation 512 and output a corresponding signal before the second detector 506B since the shorter wavelengths permitted by the second bandpass filter 504E may be associated with higher temperatures resulting from higher pulse energies of the therapeutic radiation 510. Accordingly, detection signals output by the first and second detectors 506A, 506B that each represents the intensity of a given wavelength band of the thermal radiation 512, and/or the ratios of the intensities or other relationships therebetween may be used to determine the temperature of the eye 100.

In the systems 500A, 500B (hereinafter "systems 500"), detector efficiency of each of the detectors 506, 506A, 506B may vary with wavelength, which may be corrected and/or calibrated for. Alternatively or additionally, there may be some IR absorption, e.g., absorption of at least some spectral components of the thermal radiation 512, by parts of the eye 100 such as the aqueous humor which may be corrected and/or calibrated for. In some embodiments, IR absorption by parts of the eye 100 may be avoided, or at least reduced, by detecting predetermined wavelengths or wavelength ranges of the thermal radiation 512 that do not experience significant absorption by any parts of the eye 100.

For any given discrete pulse of therapeutic radiation 510 that is absorbed by and causes the eye 100 to emit thermal radiation 512, the detectors 506, 506A, and/or 506B may in some embodiments detect and/or compare relative intensities of the thermal radiation 512 at multiple different wavelengths to determine the temperature of the eye 100. FIG. 5B illustrates one arrangement involving two detectors that can be implemented to detect multiple different wavelengths of the thermal radiation 512 emitted responsive to a single discrete pulse of the therapeutic radiation 510, but other arrangements can alternatively or additionally be implemented. For instance, the system 500A of FIG. 5A may be modified to include, e.g., a split signal path for the thermal radiation 512 with an optical delay line in one of two branches and a different bandpass filter in each of the two branches to allow a single detector such as the detector 506 to detect multiple different wavelengths of the thermal radiation 512 emitted responsive to a single discrete pulse of the therapeutic radiation 510.

Alternatively or additionally, the detectors 506, 506A, and/or 506B of FIGS. 5A and 5B may each generate absolute measurements at a single wavelength or wavelength band, in which case quantum efficiency of the detectors 506, 506A, and/or 506B may be used together with the measurements to determine the temperature of the eye 100.

Alternatively or additionally, thermal radiation 512 intensity may be determined as a ratio with therapeutic radiation 512 pulse energy and/or as a ratio with an initial reference temperature (e.g., initial body temperature and/or initial temperature of the eye 100).

Alternatively or additionally, black body radiation, e.g., the thermal radiation 512, may be detected and/or measured as a relative reading. In one example, a baseline blackbody radiation level is measured prior to exposure to the therapeutic radiation 510. Measurement of the baseline blackbody radiation level may be determined to correspond to a body temperature of 310.15 K (37 C). A change in the response of the detector 506, 506A, and/or 506B after exposure of the eye 100 to the therapeutic radiation 510 may provide a calibrated indication of the treated tissue temperature.

In a further example, a readout of the detector 506, 506A, and/or 506B may be synchronized to pulses of the therapeutic radiation 510. In this case for each pulse of the therapeutic radiation 510 the detector 506, 506A, and/or 506B may provide a reading at a defined time delay corresponding to body temperature constants as well as the therapeutic and measurement system dynamics. The reference may be taken from the thermal radiation 512 prior to the first pulse of the therapeutic radiation 510. The rise of temperature due to each pulse of the therapeutic radiation 510 may be monitored and the system 500A and/or 500B can stop after a pulse of the therapeutic radiation 510 has provided the required and/or desired temperature at the eye 100.

Figure 6:
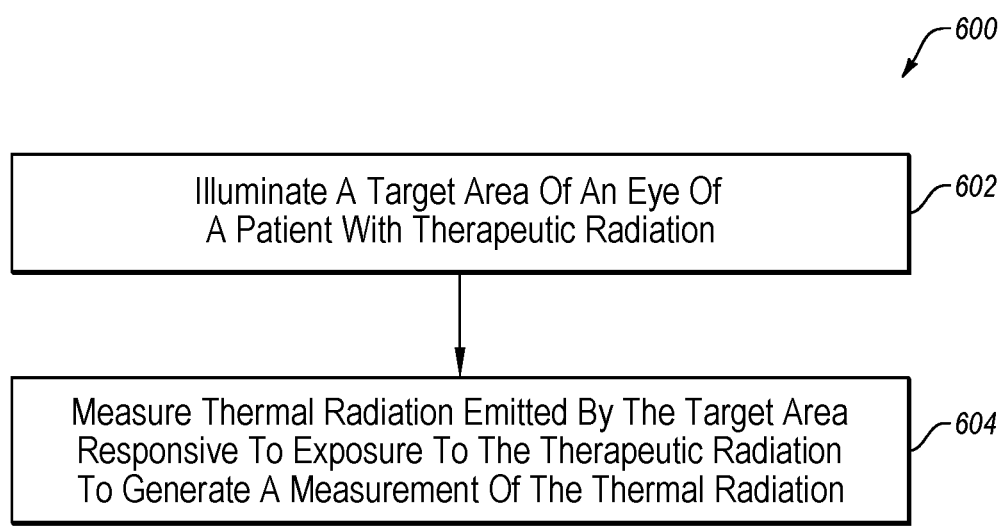
FIG. 6 illustrates a flow diagram of an example method to measure therapeutic radiation dosimetry.

FIG. 6 illustrates a flow diagram of an example method 600 to measure therapeutic radiation dosimetry, arranged in accordance with at least some embodiments described herein. The method 600 may be performed, in whole or in part, in the systems 400, 500 and/or in other systems and configurations. Alternatively or additionally, the method 600 may be implemented by a processor device, such as the processor device 508, that performs or controls performance of one or more of the operations of the method 600. For instance, a computer (such as the computing device 700 of FIG. 7) or other processor device may be included in and/or communicatively coupled to the system 400, 500A, or 500B and may execute software or other computer-readable instructions accessible to the computer, e.g., stored on a non-transitory computer-readable medium accessible to the computer, to perform or control the system 400, 500A, or 500B to perform the method 600 of FIG. 6.

The method 600 may include one or more of blocks 602 and/or 604. Although illustrated as discrete blocks, various blocks may be divided into additional blocks, supplemented with additional blocks, combined into fewer blocks, or eliminated, depending on the particular implementation. The method 600 may begin at block 602.

In block 602 ("Illuminate A Targeted Area Of An Eye Of A Patient With Therapeutic Radiation"), a targeted area of an eye of a patient may be irradiated with therapeutic radiation. A temperature of the targeted area may depend on a dosage of the therapeutic radiation. Block 602 may be followed by block 604.

In block 604 ("Measure Thermal Radiation Emitted By The Targeted Area Responsive To Exposure To The Therapeutic Radiation To Generate A Measurement Of The Thermal Radiation"), thermal radiation emitted by the targeted area responsive to exposure to the therapeutic radiation may be measured to generate a measurement of the thermal radiation. The measurement of the thermal radiation may be indicative of and/or may include the temperature of the targeted area and/or the dosage of the therapeutic radiation.

Measuring the thermal radiation to generate the measurement may include detecting an intensity of the thermal radiation to generate detected intensity. In these and other embodiments, the method 600 may further include calculating the temperature of the targeted area based on the detected intensity, a quantum efficiency of a detector that generates the detected intensity. Alternatively or additionally, the calculation of the temperature of the targeted area may be based on a blackbody spectrum associated with a target temperature or other temperature.

For this and other procedures and methods disclosed herein, the functions or operations performed in the processes and methods may be implemented in differing order. Furthermore, the outlined operations are only provided as examples, and some of the operations may be optional, combined into fewer operations, supplemented with other operations, or expanded into additional operations without detracting from the disclosed embodiments.

For instance, the method 600 may further include filtering an optical path between the targeted area and a detector system that measures the thermal radiation to block radiation with wavelengths associated with temperatures less than a target temperature threshold. In these and other embodiments, the method 600 may further include terminating exposure of the eye of the patient to the therapeutic radiation responsive to the measurement of the thermal radiation meeting or exceeding the target temperature threshold.

In some embodiments, irradiating the targeted area with the therapeutic radiation in the method 600 may include irradiating the targeted area with discrete pulses of the therapeutic radiation, where the discrete pulses of therapeutic radiation have different amounts of pulse energy. In these and other embodiments, measuring the thermal radiation to generate the measurement may include measuring thermal radiation in a first spectral band associated with a first temperature lower than the target temperature threshold to generate a first measurement of the thermal radiation; and measuring thermal radiation in a second spectral band associated with the target temperature threshold to generate a second measurement of the thermal radiation. Alternatively or additionally, the method 600 may further include determining a current dosage of the therapeutic radiation based on the first measurement responsive to the first measurement exceeding a first threshold and the second measurement being below a second threshold that is lower than the first threshold; determining a target dosage of the therapeutic radiation based on at least one of the current dosage, the first measurement, and the second measurement; and controlling the therapeutic radiation source to emit a discrete pulse with an amount of pulse energy that corresponds to the target dosage. In some embodiments, the method 600 may further include terminating exposure of the eye of the patient to the therapeutic radiation responsive to the therapeutic radiation source emitting the discrete pulse with the amount of pulse energy that corresponds to the target dosage.

Alternatively or additionally, the method 600 may further include synchronizing the measurement of the thermal radiation to the discrete pulses of therapeutic radiation. For instance, in the context of FIGS. 5A and/or 5B, one or more of the detectors 506, 506A, and/or 506B may be synched to the discrete pulses of the therapeutic radiation 510 such that they detect the thermal radiation 512 during time periods that include a thermal response of the targeted area of the eye 100 to the discrete pulses of therapeutic radiation 510. The time periods that include the thermal response may include time periods at which the targeted area of the eye 100 is irradiated with the discrete pulses. At other times, one or more of the detectors 506, 506A, and/or 506B may be turned off or otherwise operated to not detect the thermal radiation 512. Such a detection scheme may reduce noise in the detection signal(s) generated by the detectors 506, 506A, and/or 506B.

In at least one embodiment of the method 600, measuring the thermal radiation may include measuring the thermal radiation using a detector with a bandwidth greater than 10 megahertz (MHz) at sub microsecond temporal resolution.

Alternatively or additionally, the measurement of the thermal radiation may include one or more measurements of a temperature of the targeted area. Each of the one or more measurements may be associated with a corresponding discrete pulse of the discrete pulses of therapeutic radiation. Each of the one or more measurements may have a corresponding known amount of pulse energy. In these and other embodiments, the method 600 may further include determining a target dosage or target pulse energy of the therapeutic radiation based on the one or more measurements and the corresponding known amount of pulse energy; and controlling the therapeutic radiation source to emit a discrete pulse with an amount of pulse energy that corresponds to the target dosage. The target dosage or target pulse energy may be calculated or otherwise determined as a pulse energy of one of the discrete pulses of the therapeutic radiation effective to cause the targeted area of the eye to be heated to the target temperature threshold. The method 600 may further include terminating exposure of the eye of the patient to the therapeutic radiation responsive to the therapeutic radiation source emitting the discrete pulse with the amount of pulse energy that corresponds to the target dosage.

Figure 7:
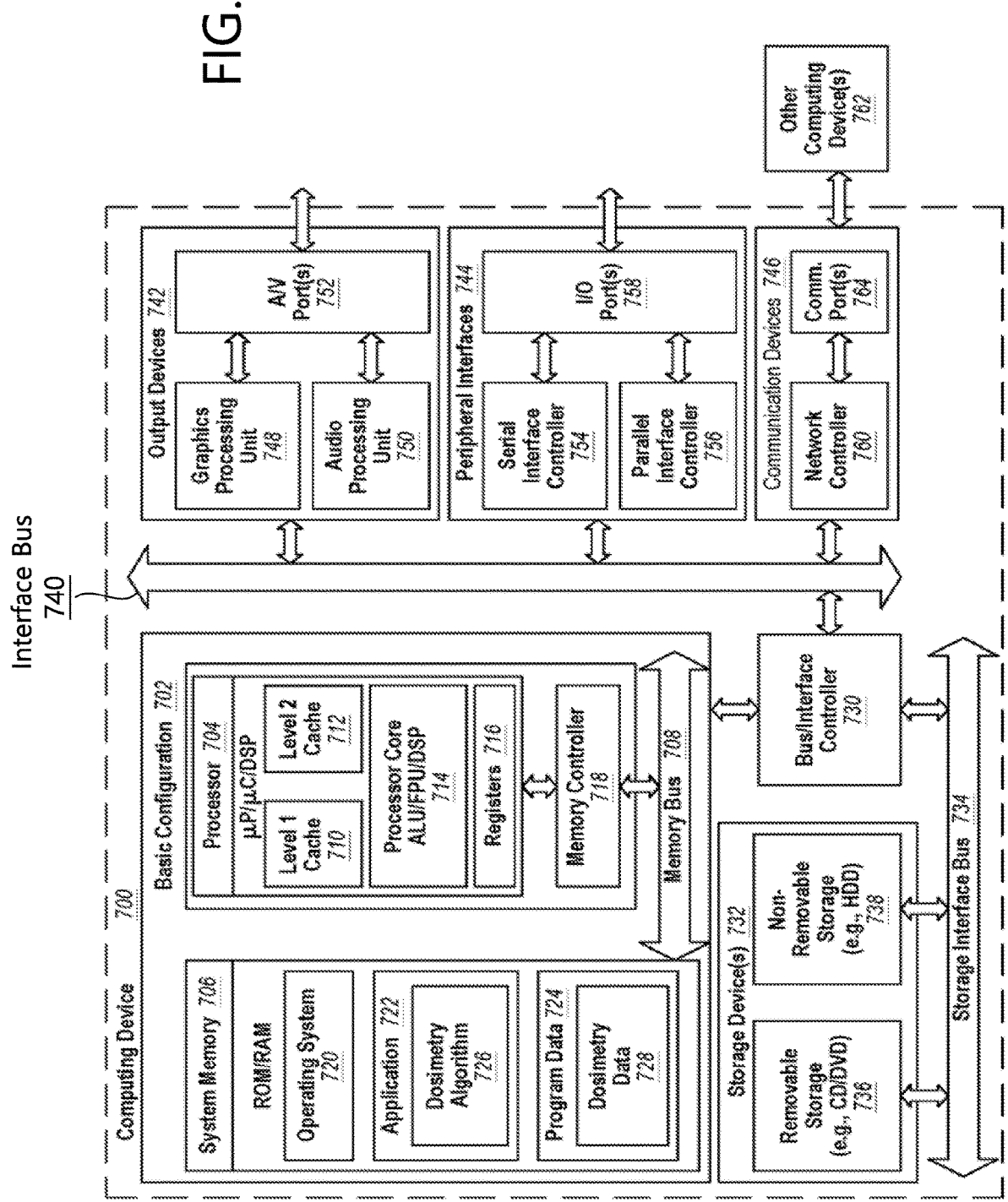
FIG. 7 illustrates a block diagram of an example computing device, all arranged in accordance with at least one embodiment of the present disclosure.

FIG. 7 illustrates a block diagram of an example computing device 700, in accordance with at least one embodiment of the present disclosure. The computing device 700 may be used in some embodiments to perform or control performance of one or more of the methods and/or operations described herein. For instance, the computing device may be communicatively coupled to and/or included in the systems 400, 500 to perform or control performance of the method 600 of FIG. 6 or other methods or processes described herein. In a basic configuration 702, the computing device 700 typically includes one or more processors 704 and a system memory 706. A memory bus 708 may be used for communicating between the processor 704 and the system memory 706.

Depending on the desired configuration, the processor 704 may be of any type including, such as a microprocessor (μP), a microcontroller (μC), a digital signal processor (DSP), or any combination thereof. The processor 704 may include one or more levels of caching, such as a level one cache 710 and a level two cache 712, a processor core 714, and registers 716. The processor core 714 may include an arithmetic logic unit (ALU), a floating point unit (FPU), a digital signal processing core (DSP Core), or any combination thereof. An example memory controller 718 may also be used with the processor 704, or in some implementations, the memory controller 718 may be an internal part of the processor 704.

Depending on the desired configuration, the system memory 706 may be of any type, such as volatile memory (such as RAM), non-volatile memory (such as ROM, flash memory, or the like), or any combination thereof. The system memory 706 may include an operating system 720, one or more applications 722, and program data 724. The application 722 may include a dosimetry algorithm 726 that is arranged to measure therapeutic radiation dosimetry. The program data 724 may include dosimetry data 728 such as values included in or derived from detection signals generated as a measurement of detected thermal radiation and/or a graph, table, equation(s), or other information that relates thermal radiation intensities, wavelengths, and/or temperatures of black bodies. In some embodiments, the application 722 may be arranged to operate with the program data 724 on the operating system 720 to perform one or more of the methods and/or operations described herein, including those described with respect to FIG. 6.

The computing device 700 may include additional features or functionality, and additional interfaces to facilitate communications between the basic configuration 702 and any other devices and interfaces. For example, a bus/interface controller 730 may be used to facilitate communications between the basic configuration 702 and one or more data storage devices 732 via a storage interface bus 734. The data storage devices 732 may include removable storage devices 736, non-removable storage devices 738, or a combination thereof. Examples of removable storage and non-removable storage devices include magnetic disk devices such as flexible disk drives and hard-disk drives (HDDs), optical disk drives such as compact disk (CD) drives or digital versatile disk (DVD) drives, solid state drives (SSDs), and tape drives to name a few. Example computer storage media may include volatile and non-volatile, removable and non-removable media implemented in any method or technology for storage of information, such as computer-readable instructions, data structures, program modules, or other data.

The system memory 706, the removable storage devices 736, and the non-removable storage devices 738 are examples of computer storage media. Computer storage media includes, but is not limited to, RAM, ROM, EEPROM, flash memory or other memory technology, CD-ROM, digital versatile disks (DVDs) or other optical storage, magnetic cassettes, magnetic tape, magnetic disk storage or other magnetic storage devices, or any other medium which may be used to store the desired information and which may be accessed by the computing device 700. Any such computer storage media may be part of the computing device 700.

The computing device 700 may also include an interface bus 740 for facilitating communication from various interface devices (e.g., output devices 742, peripheral interfaces 744, and communication devices 746) to the basic configuration 702 via the bus/interface controller 730. The output devices 742 include a graphics processing unit 748 and an audio processing unit 750, which may be configured to communicate to various external devices such as a display or speakers via one or more A/V ports 752. The peripheral interfaces 744 include a serial interface controller 754 or a parallel interface controller 756, which may be configured to communicate with external devices such as input devices (e.g., keyboard, mouse, pen, voice input device, touch input device, and/or others), sensors, or other peripheral devices (e.g., printer, scanner, and/or others) via one or more I/O ports 758. The communication devices 746 include a network controller 760, which may be arranged to facilitate communications with one or more other computing devices 762 over a network communication link via one or more communication ports 764.

The network communication link may be one example of a communication media. Communication media may typically be embodied by computer-readable instructions, data structures, program modules, or other data in a modulated data signal, such as a carrier wave or other transport mechanism, and may include any information delivery media. A "modulated data signal" may be a signal that includes one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR), and other wireless media. The term "computer-readable media" as used herein may include both storage media and communication media.

The computing device 700 may be implemented as a portion of a small-form factor portable (or mobile) electronic device such as a cell phone, a personal data assistant (PDA), a personal media player device, a wireless web-watch device, a personal headset device, an application-specific device, or a hybrid device that include any of the above functions. The computing device 700 may also be implemented as a personal computer including both laptop computer and non-laptop computer configurations.

The present disclosure is not to be limited in terms of the particular embodiments described herein, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of this disclosure. It is also to be understood that the terminology used herein is for the purpose of describing particular embodiments only, and is not intended to be limiting.

The present disclosure is not to be limited in terms of the particular embodiments described herein, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of this disclosure. Also, the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that include A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that include A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

For any and all purposes, such as in terms of providing a written description, all ranges disclosed herein also encompass any and all possible sub ranges and combinations of sub ranges thereof. Any listed range can be easily recognized as sufficiently describing and enabling the same range being broken down into at least equal halves, thirds, quarters, fifths, tenths, and/or others. As a non-limiting example, each range discussed herein can be readily broken down into a lower third, middle third and upper third, etc. All language such as "up to," "at least," and the like include the number recited and refer to ranges which can be subsequently broken down into sub ranges as discussed above. Finally, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, various embodiments of the present disclosure have been described herein for purposes of illustration, and various modifications may be made without departing from the scope and spirit of the present disclosure. Accordingly, the various embodiments disclosed herein are not intended to be limiting.

What is claimed is:

1. A laser-based ophthalmological surgical system, comprising:
   a radiation source configured to emit therapeutic radiation, the therapeutic radiation including a discrete pulse that has a particular pulse frequency and an amount of pulse energy corresponding to a dosage of the therapeutic radiation;
   one or more optical elements configured to direct the therapeutic radiation to a targeted area of an eye of a patient, wherein a temperature of the targeted area depends on the dosage of the therapeutic radiation; and
   a detector system configured to measure thermal radiation emitted by the targeted area responsive to exposure to the therapeutic radiation, wherein the detector system includes a first detector configured to detect thermal radiation at a first wavelength and a second detector configured to detect thermal radiation at a second wavelength shorter than the first wavelength, wherein the one or more optical elements are configured to optically couple the detector system to the targeted area, wherein the radiation source emits a plurality of therapeutic radiations to one targeted area, and the detector system measures thermal radiation at a certain time for each of the plurality of therapeutic radiations, the certain time having a defined time delay from an emitting time of each of the plurality of therapeutic radiations and corresponding to a thermal response of the one targeted area, wherein the first wavelength corresponds to a first temperature lower than a target temperature threshold, and the second wavelength corresponds to the target temperature threshold, wherein at least one of the first wavelength or the second wavelength is in a range from 1000 nm to 2000 nm, and wherein the temperature of the targeted area is determined based on both thermal radiation detected by the first detector and the thermal radiation detected by the second detector.

2. The laser-based ophthalmological surgical system of claim 1, wherein at least one of the first detector or the second detector comprises:

a detector with a quantum efficiency, the detector configured to detect an intensity of the thermal radiation; and a processor device communicatively coupled to the detector and configured to:

receive the detected intensity from the detector; and calculate the temperature of the targeted area based on the detected intensity, the quantum efficiency of the detector, and a blackbody spectrum associated with the target temperature threshold of the targeted area.

3. The laser-based ophthalmological surgical system of claim 1, wherein at least one of the first detector or the second detector includes an infrared (IR) detector.

4. The laser-based ophthalmological surgical system of claim 1, wherein at least one of the first detector or the second detector comprises an infrared (IR) detector, wherein the IR detector includes an indium gallium sulfide (InGaS) IR detector, a mercury cadmium telluride (MCT) IR detector, or an indium phosphide (InP) IR detector.

5. The laser-based ophthalmological surgical system of claim 1, wherein the one or more optical elements include at least one filter positioned in an optical path between the targeted area and the detector system, wherein the filter is configured to block radiation with a wavelength less than one micrometer.

6. The laser-based ophthalmological surgical system of claim 1, wherein at least one of the first detector or the second detector includes a bandwidth greater than 10 megahertz (MHz) and is configured to measure the thermal radiation at sub microsecond temporal resolution.

7. The laser-based ophthalmological surgical system of claim 1, wherein the one or more optical elements include at least one beam splitter, wherein the at least one beam splitter is configured to provide the first wavelength to the first detector and provide the second wavelength to the second detector.

8. The laser-based ophthalmological surgical system of claim 1, wherein the one or more optical elements comprise:

a first filter positioned in a first optical path between the targeted area and the first detector, wherein the first filter is configured to pass radiation at the first wavelength to the first detector; and a second filter positioned in a second optical path between the targeted area and the second detector, wherein the second filter is configured to pass radiation at the second wavelength to the second detector.

9. The laser-based ophthalmological surgical system of claim 1, further comprising a processor device communicatively coupled to the radiation source and the detector system, wherein the processor device is configured to terminate exposure of the targeted area of the eye of the patient to the therapeutic radiation responsive to a measurement of the thermal radiation generated by the detector system reaching or exceeding the target temperature threshold.

10. The laser-based ophthalmological surgical system of claim 1, wherein the first detector includes a first bandpass filter having a center wavelength corresponding to the first wavelength, and the second detector includes a second bandpass filter having a center wavelength corresponding to the second wavelength.

* * * * *